United States Patent [19]

Ramachandran et al.

[11] Patent Number: 5,278,319

[45] Date of Patent: Jan. 11, 1994

[54] PROCESS FOR THE PRODUCTION OF HYDROCARBON PARTIAL OXIDATION PRODUCTS

[75] Inventors: Ramakrishnan Ramachandran, Allendale; Loc Dao, Bound Brook; Donald L. MacLean, Clinton, all of N.J.

[73] Assignee: The BOC Group, Inc., New Providence, N.J.

[21] Appl. No.: 868,594

[22] Filed: Apr. 14, 1992

Related U.S. Application Data

[63] Continuation-in-part of Ser. No. 613,437, Nov. 14, 1990, abandoned, and a continuation-in-part of Ser. No. 693,207, Apr. 30, 1991, abandoned.

[51] Int. Cl.$^5$ ............... C07D 307/33; C07D 307/89
[52] U.S. Cl. .................. 549/249; 549/231; 549/232; 549/233; 549/247; 549/248; 549/250; 549/262; 558/319; 558/320; 500/241.1; 562/512.2; 568/398.8; 568/469.9; 568/840; 568/841; 568/910.5
[58] Field of Search ............... 549/231–233, 256, 257, 259, 261, 262, 249, 250, 247, 248; 568/840, 841, 910.5, 469.9, 393.8; 423/415; 563/512.2; 560/241.1; 558/319, 320

[56] References Cited

U.S. PATENT DOCUMENTS

| | | | |
|---|---|---|---|
| 3,868,400 | 2/1975 | Norton | 558/319 |
| 3,904,652 | 9/1975 | Frank | 549/260 |
| 4,000,178 | 12/1976 | Kahney et al. | 558/319 |
| 4,118,402 | 10/1978 | Suzuki et al. | 549/257 |
| 4,127,591 | 11/1978 | Kamimura et al. | 549/257 |
| 4,316,856 | 2/1982 | Guttmann et al. | 558/319 X |
| 4,322,368 | 3/1982 | Guttmann et al. | 558/319 X |
| 4,339,394 | 7/1982 | Grasselli et al. | 558/319 X |
| 4,754,049 | 6/1988 | Khoobiar et al. | 558/319 X |
| 4,849,538 | 7/1989 | Ramachandran | 558/319 |
| 4,863,330 | 9/1989 | Ramachandran | 558/319 X |
| 4,870,201 | 9/1989 | Ramachandran | 558/319 |
| 4,943,650 | 7/1990 | Ramachandran | 558/319 |
| 4,987,239 | 11/1991 | Ramachandran | 549/262 |
| 5,015,756 | 5/1991 | Ramachandran | 558/319 X |
| 5,126,463 | 6/1992 | Ramachandran | 549/247 |

*Primary Examiner*—Cecilia Tsang
*Attorney, Agent, or Firm*—Coleman R. Reap; Larry R. Cassett

[57] ABSTRACT

An improved process is provided for the production of a partial oxidation product by the vapor phase reaction of a hydrocarbon with substantially pure oxygen in the presence of a suitable catalyst. In the improved process, the partial oxidation product is removed, carbon dioxide and excess carbon monoxide, present in the reactor effluent as by-products, are also removed and the remaining gaseous effluent, comprised mainly of carbon monoxide and unreacted hydrocarbon, is recycled to the reactor. The concentration of carbon monoxide throughout the system is maintained sufficiently high to prevent the formation of a flammable mixture in the reactor or associated equipment.

19 Claims, 1 Drawing Sheet

PROCESS FOR THE PRODUCTION OF HYDROCARBON PARTIAL OXIDATION PRODUCTS

RELATED APPLICATIONS

This is a continuation-in-part of Ser. No. 07/613,437, filed Nov. 14, 1990, now abandoned and Ser. No. 07/693,207 filed Apr. 30, 1991, now abandoned.

FIELD OF THE INVENTION

The present invention is directed to a process for producing partial oxidation products by the reaction of a hydrocarbon and an oxygen-containing gas in the presence of a suitable catalyst, and more particularly to a process for reducing or eliminating the hazard of an explosion or fire in a vapor phase reactor system in which a hydrocarbon partial oxidation product is produced from a hydrocarbon and oxygen.

BACKGROUND OF THE INVENTION

Certain partial oxidation products are produced commercially by the oxidation of an appropriate hydrocarbon in the vapor phase over a suitable catalyst. For example, cyclic anhydrides are produced commercially by the vapor phase catalytic partial oxidation of aromatic hydrocarbons, such as o-xylene or benzene, or straight-chain hydrocarbons, such as n-butane or butene, in the presence of an oxygen-containing gas, over a vanadium-containing catalyst. Similarly, nitriles, alkylene oxides, aldehydes and halogenated hydrocarbons are produced by the partial oxidation of appropriate alkanes and alkenes in the presence of selected catalysts. Air is generally used as the oxygen-containing gas, because of its low cost and ready availability. The reaction can be carried out in any suitable reactor, such as a fixed bed, fluidized bed, moving bed, trickle bed or transport bed, and it produces the partial oxidation product, and generally carbon monoxide (CO), carbon dioxide ($CO_2$), water, and smaller amounts of other partially oxidized by-products. The reaction equipment train generally consists of a reactor, in which the partial oxidation product is produced, a scrubber, in which the partial oxidation product is scrubbed from the reactor effluent gases by means of water or other solvent for the partial oxidation product, and means for further treating the scrubbed effluent gases.

In the past it was common to practice the above-described process on a single pass basis with the conversion of hydrocarbon to the desired product being maximized. This resulted in a low overall efficiency, since the selectivity to partial oxidation product was below the maximum. Consequently, the scrubber effluent gas contained, in addition to unreacted hydrocarbon, considerable amounts of CO and $CO_2$. These products were usually incinerated, so that the only return realized from them was heat value. In later processes a portion of the scrubber effluent gas was recycled, the conversion of the hydrocarbon feedstock was lowered and the selectivity of hydrocarbon conversion to the desired partial oxidation product was maximized. The remainder of the effluent was purged from the system to prevent the build-up of CO, $CO_2$ and nitrogen (introduced into the system when air is used as the source of oxygen). These improvements resulted in a reduced "per pass" conversion but the overall efficiency of the process was increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent, maleic anhydride is recovered from the reactor effluent gas stream and a portion of the remaining stream is recycled. This patent also teaches recovering butane by temperature swing adsorption from the non-recycled gas stream and recycling the recovered butane to the reactor.

A major problem associated with the gas phase production of partial oxidation products by the oxidation of hydrocarbons with an oxygen-containing gas is that since the reaction is carried out at elevated temperatures, there is an ever-present danger of a fire or an explosion in the reactor, or the equipment or pipelines associated with the reactor, as a result of the decomposition of unreacted hydrocarbons. The propensity of the hydrocarbons to decompose is enhanced by the presence of catalyst, and the tendency toward decomposition is particularly enhanced in fluidized bed or transport bed reactors. Accordingly, the concentrations of the reactants in the system are maintained such that the mixture is kept outside of the flammability range. Although nitrogen serves to reduce the flammable mixture range when air is used as the source of oxygen for the reaction, the flammable mixture range for hydrocarbon-air mixtures is still quite broad. Consequently, it has been customary to operate gas phase partial oxidation product reactors at low hydrocarbon levels, so that the reaction mixture will remain outside of the flammable range.

U.S. Pat. No. 3,904,652 teaches a gas phase maleic anhydride manufacturing process in which oxygen is used as the oxidizing gas and an inert gas, such as nitrogen, argon, helium or a lower hydrocarbon is fed into a fixed bed reactor with the n-butane and oxygen, the inert gas serving as a diluent to reduce the concentrations of oxygen and butane in the reactor to below the point at which they form a flammable mixture. In the disclosed process, a portion of the gaseous effluent, which contains, in addition to butane, carbon monoxide, carbon dioxide and the inert gas, is recycled. One of the disadvantages of the process of this patent is that recycling carbon monoxide with the other gases increases the fire and explosion hazard at the reactor inlet because carbon monoxide itself is highly flammable.

U.S. Pat. No. 4,352,755 discloses a recycle process for the vapor phase manufacture of maleic anhydride by reacting a straight-chain $C_4$ hydrocarbon with oxygen in the presence of $CO_2$. In the process disclosed in this patent the gaseous mixture may contain up to 30 volume percent of carbon dioxide as the inert diluent and contains at least 25 volume percent $C_4$ hydrocarbon This patent states that at most 2% v/v and more preferably at most 1% v/v of carbon monoxide is present in the oxidation stage. In the process of this patent, the presence of large amounts of $C_4$ hydrocarbon can render the gas mixture in the system flammable, especially in the region of the reactor outlet.

U.S. Pat. No. 3,868,400, issued to Norton, discloses that in the vapor phase ammoxidation of alkyl-substituted organic compounds the yield of nitrile product can be increased and ammonia and hydrocarbon burn mitigated by incorporating carbon monoxide into the reactant stream to the ammoxidation reaction system.

As is well known, under a given set of conditions of temperature and pressure the flammability of a gaseous hydrocarbon-oxygen mixture is dependent upon the ratio of the gaseous components in the mixture. At very low hydrocarbon concentrations the gas mixture is nonflammable, but at a certain hydrocarbon concentration threshhold level, usually referred to as the lower explosive limit (LEL), the mixture becomes flammable and remains flammable with increasing hydrocarbon concentrations until the hydrocarbon level reaches a certain level, often referred to as the upper explosive limit (UEL) of the gas mixture. The explosive range of a gaseous fuel-oxygen mixture rapidly expands as the temperature of the system increases. Even though it might otherwise be desirable to operate a gaseous partial oxidation product manufacturing process at hydrocarbon concentrations in the explosive range, it is dangerous to do so because of the hazard of fire or explosion in the reactor or associated equipment. The present invention permits optimization of the selectivity and yield of the process, even while operating the process at hydrocarbon concentrations normally falling within the flammable mixture range. In the past, this was not considered possible.

SUMMARY OF THE INVENTION

The present invention provides an improvement in a recycle process and apparatus for manufacturing partial oxidation products, such as aldehydes, alkylene oxides, halogenated hydrocarbons and nitriles, by the vapor phase oxidation of selected hydrocarbons with oxygen in the presence of suitable catalysts, recovering the partial oxidation product from the gaseous reactor effluent and recycling unreacted hydrocarbon to the reaction zone. The invention comprises maintaining the concentration of carbon monoxide in all parts of the system sufficiently high that the level of fuel components in the mixture is always above the level at which a flammable mixture exists. This is conveniently accomplished by removing carbon dioxide from the partial oxidation product-free effluent and recycling the resulting carbon monoxide-enriched stream to the feed inlet or to the feed outlet of the hydrocarbon oxidation reactor. Unreacted hydrocarbon can be recycled to the feed inlet of the hydrocarbon reactor with the carbon-monoxide rich recycle stream. Alternatively, the unreacted hydrocarbon can be removed from the effluent and recycled to the inlet of the hydrocarbon reactor and the carbon monoxide-rich stream can be recycled to the downstream side of the reactor.

According to one embodiment of the process of the invention, one or more hydrocarbon partial oxidation product precursors are contacted with an oxygen-containing gas in the vapor phase in a suitable oxidation reactor and in the presence of carbon monoxide as the principal gaseous component, to produce a gaseous product stream containing one or more partial oxidation products, the specific partial oxidation product produced depending upon which hydrocarbon or hydrocarbons are reacted, the particular catalyst used and, in some cases, the presence of other reactants. The hydrocarbon oxidation reactor product stream also contains carbon monoxide and carbon dioxide, and generally unreacted hydrocarbon(s), oxygen, and possibly small amounts of other reaction by-products. The gaseous product stream leaving the oxidation reactor is treated in a partial oxidation product removal means, such as a partial oxidation product condenser or a scrubber in which the partial oxidation product is contacted with a liquid solvent which removes substantially all of the partial oxidation product from the gas stream. The partial oxidation product-containing liquid is discharged from the partial oxidation product removal means and treated to recover the partial oxidation product. All or a portion of the partial oxidation product-free gaseous product stream is then treated in a carbon dioxide separator which removes some or all of the carbon dioxide, and which also removes carbon monoxide in excess of the amount that it is desired to maintain in the system. The remainder of the gaseous effluent, comprised predominantly of carbon monoxide and unreacted hydrocarbon, is recycled to the inlet of the hydrocarbon oxidation reactor.

In an alternate embodiment of the process of the invention the gaseous effluent from the scrubber is treated in a hydrocarbon separator to remove substantially all of the unreacted hydrocarbon from the scrubbed gas stream and the separated unreacted hydrocarbon is recycled to the hydrocarbon oxidation reactor inlet. All or a portion of the hydrocarbon-depleted effluent from the hydrocarbon separator is then treated in a carbon dioxide separator to remove carbon dioxide and excess carbon monoxide from the stream and the remainder of the stream, now rich in carbon monoxide, is recycled to either the inlet or the outlet of the hydrocarbon oxidation reactor, or to both, if desired.

In a preferred embodiment of the process aspect of the invention the oxygen-containing gas is substantially pure oxygen. In another preferred embodiment carbon dioxide is removed from the scrubber effluent by adsorption, absorption or membrane separation. In another preferred embodiment the hydrocarbon reactant contains 2 to 12 carbon atoms; in a more preferred embodiment the hydrocarbon is selected from alkanes and alkenes having 2 to 12 carbon atoms or from aromatic hydrocarbons having up to 12 carbon atoms; and in the most preferred embodiment, the hydrocarbon is selected from alkanes and alkenes having 2 to 6 carbon atoms or aromatic hydrocarbons having up to 10 carbon atoms.

Another novel aspect of the invention is the system in which one embodiment of the process of the invention is carried out. The system comprises a vapor phase hydrocarbon reactor, a partial oxidation product removal means, an unreacted hydrocarbon separator, a carbon dioxide separator and connecting conduits. The hydrocarbon reactor outlet is connected to the partial oxidation product removal means. In turn, the gaseous effluent outlet from the partial oxidation product removal means is connected to the inlet of either the unreacted hydrocarbon separator or the carbon dioxide separator, whichever unit is first in the equipment train. The unreacted hydrocarbon separator and the carbon dioxide separator are arranged serially in the train and either unit may precede the other. The waste gas stream outlet from the last separator in the train is connected to a vent line. In the novel system of the invention the recycle stream line from the unreacted hydrocarbon separator is connected to the inlet of the hydrocarbon reactor and the carbon monoxide recycle stream line from the carbon dioxide separator is connected to the outlet from the hydrocarbon reactor.

DETAILED DESCRIPTION OF THE INVENTION

Figure 1:
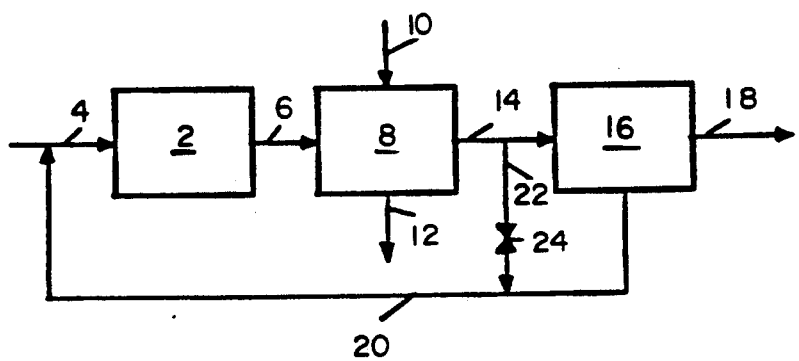
FIG. 1 illustrates, in a block diagram, one embodiment of a system for producing a partial oxidation product in accordance with the present invention.

According to the process of the invention, a hydrocarbon in the gaseous state is reacted with oxygen in a reaction zone containing a suitable catalyst and in the presence of carbon monoxide as the principal gaseous component to produce a gaseous product stream containing a partial oxidation product as the desired product, carbon monoxide and carbon dioxide as by-products and usually unreacted hydrocarbon and oxygen; the partial oxidation product is recovered from the gaseous product stream; unreacted hydrocarbon is recycled to the reaction zone and carbon monoxide is recycled to the inlet or the outlet of the hydrocarbon reactor. The term "partial oxidation product", as used herein, means a chemical compound other than carbon monoxide and carbon dioxide that is produced by the reaction of a hydrocarbon with oxygen, and optionally, one or more other reactants.

The process of the invention can be used for the manufacture of any partial oxidation product that is produced by the gas phase reaction at elevated temperatures of a hydrocarbon with oxygen. Typical partial oxidation product manufacturing processes in which the invention can be employed are:

1. The manufacture of cyclic anhydrides by the reaction of aromatic compounds or straight-chained $C_4$ hydrocarbons with oxygen in the presence of a suitable catalyst. Examples include the production of maleic anhydride by the reaction of benzene or a saturated or unsaturated $C_4$ hydrocarbon such as butane or butene with oxygen and the manufacture of phthalic anhydride by the reaction of o-xylene or naphthalene with oxygen.

2. The manufacture of alkylene oxides by the reaction of lower alkanes or alkenes with oxygen in the presence of a silver oxide catalyst supported on silica or alumina or mixed molten nitrate salts. An examples is the reaction of propane or propylene with oxygen in the presence of molten sodium and potassium nitrates to produce propylene oxide.

3. The manufacture of chlorinated hydrocarbons by the reaction of lower alkanes or alkenes with oxygen and hydrogen chloride or chlorine in the presence of a copper chloride catalyst supported on silica or alumina. Examples include the reaction of ethylene or ethane with hydrogen chloride or chlorine to produce vinyl chloride or ethylene dichloride.

4. The manufacture of aldehydes by the reaction of lower alkanes or alkenes with oxygen in the presence of various metal halides or metal oxide catalysts. Examples include the production of acetaldehyde by the reaction of ethylene with oxygen in the presence of copper chloride and palladium chloride, and the manufacture of acrolein by the reaction of propane or propylene with oxygen over a molybdenum-bismuth-iron catalyst.

5. The manufacture of olefinically unsaturated nitriles by the reaction of lower alkanes or alkenes with oxygen and ammonia in the presence of a bismuth molybdenum oxide catalyst or an iron antimony oxide catalyst supported on silica or alumina. Examples of this type of process include the reaction of propane or propylene with oxygen and ammonia to produce acrylonitrile and the reaction of i-butane or i-butylene with oxygen and ammonia to produce methacrylonitrile.

As is apparent from the above examples, the process of the invention can be used for the manufacture of various partial oxidation products in the above-mentioned classes by the reaction of appropriate hydrocarbons with oxygen. The particular partial oxidation reaction that is carried out in the process of the invention is not critical to the invention. In general, the process of the invention can include any hydrocarbon partial oxidation reaction that is carried out in the vapor phase at elevated temperatures to produce any of the above partial oxidation products and which involves the reaction of a hydrocarbon and oxygen (and, where appropriate, other reactants, such as ammonia, when the partial oxidation is ammoxidation, and hydrogen chloride or chlorine, when the partial oxidation is oxychlorination) in the presence of a catalyst to produce the partial oxidation product as the main product and carbon dioxide and carbon monoxide as byproducts.

The particular hydrocarbon or hydrocarbons used as reactant in the hydrocarbon oxidation step of the process of the invention will be determined by the particular partial oxidation product that is being produced. In general, the feed hydrocarbon may be aromatic, aliphatic or cycloaliphatic, and it may be saturated or ethylenically unsaturated and straight chain or branched. Suitable aromatic hydrocarbons include those having up to twelve or more carbon atoms and suitable aliphatic and cycloaliphatic hydrocarbons include those having two to twelve or more carbon atoms. Preferred aromatic hydrocarbons are those having six to ten carbon atoms, such as benzene, o-xylene and naphthalene, and preferred aliphatic hydrocarbons are the saturated or ethylenically unsaturated straight-chain hydrocarbons having two to six hydrocarbon atoms, such as ethane, ethene, propane, propylene, n-butane, i-butane, n-butylene, i-butylene, butadiene, and the pentanes, pentenes, hexanes and hexenes.

The process of the invention will be described with particular reference to the manufacture of maleic anhydride from n-butane, but the invention is not limited thereto.

The oxygen-containing gas may be air, oxygen-enriched air, other oxygen-inert gas mixtures or substantially pure oxygen. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. Pure oxygen is preferred since its use avoids the introduction of inert gases such as nitrogen and argon into the system, and the subsequent need to remove excess quantities of these inert gases from the product gas stream to prevent their buildup in the system.

The invention can be better understood from the accompanying drawings in which the same reference numerals are used to designate the same or similar pieces of equipment in different figures. Auxiliary equipment, including compressors, heat exchangers and valves not necessary for an understanding of the invention, have been omitted from the drawings to simplify discussion of the invention.

Considering first FIG. 1, the apparatus of this embodiment includes a hydrocarbon oxidation reactor 2 having a feed inlet means 4 and a product outlet line 6. Product outlet line 6 is connected to a partial oxidation product recovery unit 8, which may be a condenser or a scrubber which receives a scrubbing liquid through inlet line 10 and discharges a liquid product through outlet line 12. Product recovery means 8 is also equipped with a partial oxidation product-free gas outlet line 14 which communicates with carbon dioxide separator 16. Separator 16 is provided with a waste gas discharge line 18, and it is also connected via recycle line 20 with feed inlet means 4. The system of FIG. 1 can also be equipped with a bypass line 22, controlled by valve 24.

Reactor 2 may be any suitable reactor but it is usually of the fixed, moving, fluidized, trickle or transport catalyst bed design. Reactor 2 may be equipped with heat exchange means (not shown) to remove heat developed in the reaction, which is exothermic. The specific design details of suitable reactors are well known and they form no part of the present invention. When partial oxidation product recovery unit 8 is a gas scrubber, i.e. an absorber, it is usually of the packed bed design, and it is here illustrated as equipped with means for spraying water or an aqueous or nonaqueous liquid on the product gas entering this unit from reactor 2. Carbon dioxide separator 16 serves to remove carbon dioxide and other inert gases from the gaseous effluent from the partial oxidation product removal means and this unit can be any device which will accomplish this result. Separator 16 is usually an adsorber, an absorber or a membrane separation unit. In preferred embodiments of the invention, separator 16 is a pressure swing adsorption (PSA) unit or a temperature swing adsorption (TSA) unit.

Figure 2:
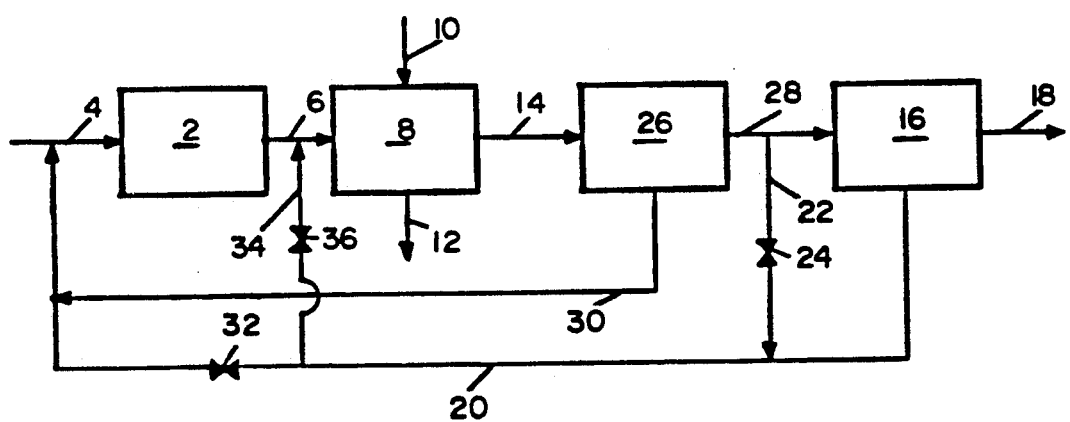
FIG. 2 illustrates, in a block diagram, an alternate embodiment of the system illustrated in FIG. 1.

FIG. 2 illustrates a variation of the system of FIG. 1. In the embodiment of FIG. 2, the equipment train includes a hydrocarbon separator 26, and the piping arrangement has been modified. Hydrocarbon separator 26 can be any suitable device that is capable of selectively removing gaseous hydrocarbon from a gas mixture. Suitable separators include adsorbers and absorbers. In preferred embodiments, separator 26 is a PSA unit or a TSA unit. Additional details concerning separators 16 and 26 are provided below.

In the piping arrangement of FIG. 2, Line 14 connects the outlet from scrubber 8 to the inlet to unreacted hydrocarbon separator 26, line 28 connects the outlet from unreacted hydrocarbon separator 26 to the inlet to carbon dioxide separator 16 and recycle line 30 connects hydrocarbon separator 26 to feed inlet means 4. Additionally, bypass line 22, controlled by valve 24, connects line 28 to recycle line 20; bypass line 34, controlled by valve 36, connects recycle line 20 to line 6; and valve 32 controls the rate of flow of fluid through line 20 to inlet means 4.

As indicated above, separators 16 and 26 can be any means for separating the desired component (unreacted hydrocarbon or carbon monoxide or both) from the scrubbed gas stream, but in the most preferred embodiment these devices are pressure swing adsorption units. Pressure swing adsorption is a well known process for separating the components of a mixture of gases by virtue of the difference in the degree of adsorption among them on a particulate adsorbent retained in a stationary bed. Typically, two or more such beds are operated in a cyclic process comprising adsorption under relatively high pressure and desorption or bed regeneration under relatively low pressure or vacuum. The desired component or components may be obtained during either of these stages. The cycle may contain other steps in addition to the fundamental steps of adsorption and regeneration, and it is commonplace to have two or more adsorbent beds cycled 180° out of phase to assure a pseudo continuous flow of desired product. While it is conventional for the adsorption step of a PSA cycle to be carried out under pressure, it can run at ambient pressure with desorption under vacuum.

In the process of the invention practiced in the FIG. 1 system, feed, comprising a suitable hydrocarbon, an oxygen-containing gas and the recycle gas stream, enters reactor 2 through inlet means 4, which may comprise a single inlet line through which a mixture of the gaseous reactants and diluents is introduced into reactor 2, or it may comprise several individual inlet lines for separately introducing the reactants into the reactor. The particular inlet arrangement will generally depend upon the type of reactor used for practicing the invention. In fixed bed reactor systems the components of the feed are often mixed before they enter the reactor and are thus fed into the reactor through a single line, whereas in fluidized bed reactor systems, the components are often separately fed into the reactor.

The feed gases entering reactor 2 contact the catalyst and react to form the product gases. Any of the well known catalysts for oxidizing hydrocarbons to partial oxidation products under the specified conditions can be used in the process of the invention. Suitable catalysts include vanadia-based catalysts, such as vanadium oxides, vanadium/molybdenum oxides, vanadium/phosphorus oxides and vanadium/titanium oxides for the preparation of cyclic anhydrides; copper chloride supported on silica or alumina for the preparation of chlorinated hydrocarbons; metal halides or metal oxides for the preparation of aldehydes; bismuth molybdate for the first stage and a mixed molybdenum- tungsten-vanadium catalyst for the second stage of a two-stage process for the preparation of unsaturated carboxylic acids from alkenes; silver oxide or mixed molten nitrates for the preparation of alkylene oxides; and multicomponent molybdate catalysts or antimony-containing catalysts for the preparation of nitriles. These catalysts and their use are conventional and well known to those skilled in the manufacture of partial oxidation products. The specific hydrocarbon oxidation catalysts used in the process of the invention do not form a critical part of the invention.

The conditions of the hydrocarbon oxidation are well known and likewise form no part of the invention. Typically, the oxidation reaction is conducted at a temperature of from about 120° to 600° C., and usually from about 150° to 500° C., and at pressures typically in the range of about 2 to 500 psig, and usually from about 3 to 350 psig. The reactants are generally passed through the reactor at a velocity in the range of from about 0.5 to 5.0 ft/sec. The volume ratio of oxygen to hydrocarbon in the feed is suitably in the range of about 0.3:1 to about 50:1.

The product gas stream leaving reactor 2 contains the desired partial oxidation product as the main product, and carbon dioxide and carbon monoxide as by-products. As noted above, the product stream generally also contains unreacted hydrocarbon and oxygen, and may contain small amounts of other by-products, impurity gases and nonreactive hydrocarbons. The product gas stream leaves reactor 2 via line 6 and, if desired, may be passed through a heat exchanger (not shown) wherein it is cooled to a temperature in the range of about 30° to about 200° C. The cooled product gas stream enters partial oxidation product removal means 8, in which the partial oxidation product is removed from the gas stream. Some partial oxidation products, such as phthalic anhydride condense from the reactor effluent stream upon cooling; others, such as maleic anhydride, are best removed by means of a scrubber. When partial oxidation product removal means 8 is a scrubber, the product gases are intimately contacted with a solvent for the partial oxidation product. The solvent dissolves substantially all of the partial oxidation product in the product gas stream and the partial oxidation product-containing solution exits scrubber 8 via line 12. It is usually further treated to recover the partial oxidation product. The scrubbed gas stream leaves partial oxidation product removal means 8 through line 14 and enters separator 16.

The principal purpose of separator 16 is to prevent the build-up of carbon dioxide and other inert gases in the system. It is preferred to recycle only carbon monoxide and the unreacted hydrocarbon, so that the process can be optimized. Accordingly, if carbon dioxide is not removed, its concentration in the system will increase and may eventually dilute the carbon monoxide concentration to the point at which a flammable mixture exists. To avoid this problem, it is only necessary to remove an amount of carbon dioxide equal to the amount of carbon dioxide produced in reactor 2 in each pass.

Separator 16 also serves the purpose of removing carbon monoxide in excess of the amounts which it is desired to recycle and other inert gases from the system. Since carbon monoxide is also a by-product of the oxidation reaction it is continuously being produced. After equilibrium is reached a quantity of carbon monoxide approximately equal to the quantity produced in the oxidation step in each pass is removed by separator 16 to prevent the buildup of carbon monoxide in the system. Other inert gases, such as nitrogen and argon (introduced into the system when air is used as the source of oxygen) are also removed from the system by means of separator 16. In the latter situation, separator 16 can be a single separator or a train of separators. To prevent the buildup of nitrogen and argon in the system when air used as the source of oxygen, it is generally preferred to remove from the system substantially all of the nitrogen and argon entering reactor 2 with the fresh feed.

When the system of FIG. 1 is operated with bypass line 22 closed, the carbon monoxide to be recycled and all of the unreacted hydrocarbon exit separator 16 via recycle line 20 and are returned to the inlet side of reactor 2. In some cases it may be preferable to have part of the gas stream leaving partial oxidation product removal means 8 bypass separator 16. This can be effected by partially opening valve 24. This alternative is advantageous when it is desired to have all of the carbon monoxide destined for recycle pass through line 22. This permits separator 16 to be operated so that it removes only unreacted hydrocarbon from the stream entering the separator. Partially bypassing separator 16 is most convenient when the oxidant entering reactor 2 is substantially pure oxygen, because the stream passing through line 22 will then be substantially free of inert gases other than carbon dioxide.

The gas mixture at all points in the reaction system is made nonflammable by maintaining the concentration of carbon monoxide in the system sufficiently high to prevent the gas mixture from forming a flammable mixture. In other words, the concentration of carbon monoxide in the system is at a high enough level that the total concentration of fuel (comprised of hydrocarbon reactant and carbon monoxide) is always above the UEL for the system. In the reaction systems of the invention, the carbon monoxide is present as the principal gaseous component, i.e. carbon monoxide is present in the reaction system at a concentration greater than any other gaseous component. The carbon monoxide concentration in the system is preferably maintained sufficiently high so that it alone will prevent the gases in any part of the system from forming a flammable mixture. The concentration of carbon monoxide necessary to provide this effect will vary from system to system, but in general, this result will be attained when the carbon monoxide content of the system comprises at least 30 volume percent of the total gases in the system. In the most preferred embodiment of the invention carbon monoxide comprises at least 40 volume percent of the total gases in the system. It is also most preferred to keep the concentration of gases other than carbon monoxide and the reactant gases as low as possible in the system.

The flammability of the gas mixture at any point in the system is dependent upon the temperature of the gas mixture at that point and the relationship is such that an increase in the temperature results in an increase in the flammable range of the gas mixture. As indicated above, the temperature at which the oxidation reaction takes place is generally in the range of about 120° to 600° C. Thus, ordinarily there would be a significant hazard of fire or an explosion in the hydrocarbon oxidation reactor. It has also been discovered however, that the flammability of the gas mixture in the hydrocarbon reactor is markedly reduced by the presence of the catalyst in the reactor, so that there is actually little danger of a fire or explosion in the reactor.

The product gas stream exiting reactor 2, however, contains little or no catalyst and is still very hot from the oxidation reaction; accordingly, there would be a considerable danger that the flammable components in the product gas stream would ignite as they exit or after they exit reactor 2 and before they are cooled, were it not for the high concentration of carbon monoxide in the reactor effluent. Maintaining a high concentration of carbon monoxide throughout the system insulates the entire system from the hazard of a fire or an explosion.

It may sometimes be desirable to maintain maximum protection in the zone just downstream of the hydrocarbon oxidation reaction zone while at the same time maximizing the rate of flow of reactants through reactor 2. The embodiment illustrated in FIG. 2 is particularly adapted to effecting this result. In the process practiced in the system of FIG. 2, part or all of the carbon monoxide recycle stream can be introduced into the system at a point downstream of the reaction zone of reactor 2. This alternative is feasible because, as noted above, the oxidation catalyst itself functions as a flame arrestor in the reactor. This embodiment presents the advantage of providing the carbon monoxide at the point where it is most needed, while at the same time allowing a greater flow of reactants through reactor 2, thereby increasing the production capacity of the system. Introducing the carbon monoxide into the reactor product stream not only serves to prevent the product gas mixture from entering into the flammable mixture range, but, because the carbon monoxide is itself cool, also serves to cool the gas mixture.

In the process of the invention as practiced in the system of FIG. 2, the gaseous effluent from partial oxidation product removal means 8 is treated in hydrocarbon separator 26 to remove substantially all of the unreacted hydrocarbon from the partial oxidation product-free gas stream and the separated unreacted hydrocarbon is recycled to the inlet end of hydrocarbon oxidation reactor 2. Part or all of the hydrocarbon-depleted effluent from the hydrocarbon separator is then treated in separator 16 to remove carbon dioxide and excess carbon monoxide from the stream and the remainder of the stream, now rich in carbon monoxide, exits separator 16 via line 20 and is recycled to either the inlet to the hydrocarbon oxidation reactor by opening valve 32 and closing valve 36, or to the downstream side of reactor 2 by opening valve 36 and closing valve 32, or to both locations by opening valve 32 and valve 36. As was the case with the FIG. 1 embodiment, a portion of the scrubbed gas leaving separator 26 can be bypassed around separator 16 via line 22 by opening valve 24.

In the startup operation of the process of the invention, supplemental carbon monoxide can be initially introduced into the system with the feed or a high carbon dioxide concentration can be initially maintained in the system to insure that the gas mixture is and remains outside of the flammable range. Then, as the concentration of carbon monoxide increases the supplemental carbon monoxide or the excess carbon dioxide will gradually decrease and be totally eliminated when the system reaches the desired equilibrium state. At this point the carbon monoxide can be easily maintained in the desired range by controlling the amount of carbon monoxide recycled.

It will be appreciated that it is within the scope of the present invention to utilize conventional equipment to monitor and automatically regulate the flow of gases within the system so that it can be fully automated to run continously in an efficient manner.

An important advantage of the invention is that it permits the hydrocarbon oxidation reaction to be conducted using a hydrocarbon feed concentration that may be varied over a wider range while minimizing the risk of fire or explosion in the hydrocarbon oxidation reactor or associated equipment. Another advantage is that the oxidation reaction may be safely conducted without the use of inert gas diluents, such as nitrogen. The process of this invention is also advantageous in its simplicity, ease of operation, low capital and operating costs and substantially reduced flammability potential. The process can be run at a relatively low per pass conversion of the feed hydrocarbon to the desired product to achieve substantially improved selectivity. It will be appreciated that a system that achieves enhanced selectivity, and hence increased overall yield of a desired product, is highly advantageous.

The invention is further illustrated by the following example wherein, unless otherwise indicated, parts, percentages and ratios are on a volume basis.

EXAMPLE I

A vapor phase maleic anhydride production run was simulated in a fluidized bed reactor based on the use of a reactor system similar to the system of FIG. 1. The simulated feed to the hydrocarbon reactor is comprised of the Fresh Feed component and the Recycle Stream component. The reaction is simulated based on the use of a vapor phase hydrocarbon reactor containing a fluidized catalyst bed of vanadium phosphorous oxide and a pressure swing adsorber containing a molecular sieve adsorption bed. The various flow rates and projected results are tabulated in TABLE I.

EXAMPLE II

A vapor phase acrylonitrile production run was simulated in a fluidized bed reactor based on the use of a reactor system similar to the system of FIG. 1. The simulated feed to the hydrocarbon reactor is comprised of the Fresh Feed component and the Recycle Stream component. The reaction is simulated based on the use of a vapor phase hydrocarbon reactor containing a fluidized catalyst bed of bismuth molybdenum oxide and a pressure swing adsorber containing a molecular sieve adsorption bed. The various flow rates and projected results are tabulated in TABLE II.

TABLE I

| | Fresh Feed | | Reactor Feed[1] | | Scrubber Feed | | PSA Feed | | Recycle | | Waste | |
|---|---|---|---|---|---|---|---|---|---|---|---|---|
| Component | Moles | Vol % | Moles | Vol % | Moles | Vol % | Moles | Vol % | Moles | Vol % | Moles | Vol % |
| n-Butane | 206.9 | 19.2 | 284.4 | 8.6 | 85.3 | 2.4 | 85.3 | 3.4 | 77.5 | 3.5 | 7.8 | 2.5 |
| i-Butane | 9.6 | 0.9 | 13.2 | 0.4 | 4.0 | 0.1 | 4.0 | 0.2 | 3.6 | 0.2 | 0.4 | 0.1 |
| $O_2$ | 859.5 | 79.9 | 991.9 | 30.1 | 145.7 | 4.1 | 145.7 | 5.7 | 132.4 | 6.0 | 13.4 | 4.2 |
| $N_2$ | 0.0 | 0.0 | 0.0 | 0.0 | 0.0 | 0.0 | 0.0 | 0.0 | 0.0 | 0.0 | 0.0 | 0.0 |
| Maleic Anhydride | 0.0 | 0.0 | 0.0 | 0.0 | 127.5 | 3.6 | 0.0 | 0.0 | 0.0 | 0.0 | 0.0 | 0.0 |
| CO | 0.0 | 0.0 | 1599.5 | 48.5 | 1760.8 | 49.7 | 1760.8 | 69.4 | 1599.5 | 72.1 | 161.3 | 50.8 |
| $CO_2$ | 0.0 | 0.0 | 324.4 | 9.6 | 458.8 | 13.0 | 458.8 | 18.1 | 324.4 | 14.6 | 134.4 | 42.4 |
| $H_2O$ | 0.0 | 0.0 | 81.8 | 5.3 | 960.8 | 27.1 | 81.1 | 3.2 | 81.1 | 3.7 | 0.0 | 0.0 |
| TOTAL | 1076.1 | 100.0 | 3294.6 | 100.0 | 3543.0 | 100.0 | 2535.8 | 100.0 | 2218.5 | 100.0 | 317.3 | 100.0 |

[1] Fresh Feed plus Recycle

TABLE II

| | Fresh Feed | | Reactor Feed[1] | | Scrubber Feed | | PSA Feed | | Recycle | | Waste | |
|---|---|---|---|---|---|---|---|---|---|---|---|---|
| Component | Moles | Vol % | Moles | Vol % | Moles | Vol % | Moles | Vol % | Moles | Vol % | Moles | Vol % |
| Propane | 170.8 | 11.4 | 248.8 | 7.9 | 82.1 | 3.1 | 82.1 | 4.7 | 78.0 | 4.8 | 4.1 | 3.1 |
| Ammonia | 147.9 | 9.9 | 147.9 | 4.7 | 26.4 | 1.0 | 0.0 | 0.0 | 0.0 | 0.0 | 0.0 | 0.0 |
| $O_2$ | 1180.0 | 78.7 | 1207.8 | 38.6 | 29.4 | 1.1 | 29.4 | 1.7 | 27.9 | 1.7 | 1.5 | 1.1 |
| Acrylonitrile | 0.0 | 0.0 | 0.0 | 0.0 | 100.0 | 3.8 | 0.0 | 0.0 | 0.0 | 0.0 | 0.0 | 0.0 |
| Hydrogen Cyanide | 0.0 | 0.0 | 0.0 | 0.0 | 20.0 | 0.8 | 0.0 | 0.0 | 0.0 | 0.0 | 0.0 | 0.0 |
| Acrolein | 0.0 | 0.0 | 0.0 | 0.0 | 1.2 | 0.0 | 0.0 | 0.0 | 0.0 | 0.0 | 0.0 | 0.0 |
| Acetonitrile | 0.0 | 0.0 | 0.0 | 0.0 | 1.5 | 0.1 | 0.0 | 0.0 | 0.0 | 0.0 | 0.0 | 0.0 |
| CO | 0.0 | 0.0 | 1397.9 | 44.7 | 1471.4 | 55.7 | 1471.4 | 83.4 | 1397.8 | 85.7 | 73.6 | 55.0 |
| $CO_2$ | 0.0 | 0.0 | 127.3 | 4.1 | 227.3 | 8.6 | 181.8 | 10.3 | 127.3 | 7.8 | 54.5 | 40.8 |
| Water | 0.0 | 0.0 | 0.0 | 0.0 | 684.3 | 25.9 | 0.0 | 0.0 | 0.0 | 0.0 | 0.0 | 0.0 |

TABLE II-continued

| Component | Fresh Feed | | Reactor Feed[1] | | Scrubber Feed | | PSA Feed | | Recycle | | Waste | |
|---|---|---|---|---|---|---|---|---|---|---|---|---|
| | Moles | Vol % | Moles | Vol % | Moles | Vol % | Moles | Vol % | Moles | Vol % | Moles | Vol % |
| TOTAL | 1498.7 | 100.0 | 3129.7 | 100.0 | 2643.6 | 100.0 | 1764.7 | 100.0 | 1631.0 | 100.0 | 133.7 | 100.0 |

[1] Fresh Feed plus Recycle

Although the invention has been described with particular reference to specific experiments, these experiments are merely exemplary of the invention and variations are contemplated. For example, the reaction can be carried out under conditions that will effect the production of other partial oxidation products. Similarly, other catalysts and adsorbents and other means of gas separation can be used in the invention, if desired. Similarly, the process of the invention may be practiced in equipment arrangements other than those illustrated in the drawings. The scope of the invention is limited only by the breadth of the appended claims.

We claim:

1. A process for the production of a partial oxidation product comprising:
   (a) contacting in the vapor phase in a reaction zone a hydrocarbon containing 2 to 12 carbon atoms and an oxygen-containing gas in the presence of an appropriate oxidation catalyst and carbon monoxide as the principal gaseous component under conditions which produce a gaseous product containing said partial oxidation product, carbon monoxide and carbon dioxide;
   (b) recovering said partial oxidation product from said gaseous product;
   (c) separating carbon dioxide from the gaseous product; and
   (d) recycling the carbon dioxide-depleted gaseous product to said reaction zone, the concentration of carbon monoxide and hydrocarbon present in all parts of the system in which said process is conducted being maintained sufficiently high during said process to prevent the existence of a flammable mixture in said system.

2. A process for the production of a partial oxidation product comprising:
   (a) contacting in the vapor phase in a reaction zone a hydrocarbon containing 2 to 12 carbon atoms and an oxygen-containing gas in the presence of an oxidation catalyst and carbon monoxide as the principal gaseous component under conditions which produce a gaseous product containing said partial oxidation product, carbon monoxide and carbon dioxide;
   (b) recovering said partial oxidation product from said gaseous product;
   (c) separating unreacted hydrocarbon and carbon monoxide from the gaseous product;
   (d) recycling the separated unreacted hydrocarbon to said reaction zone; and
   (e) recycling the separated carbon monoxide to said reaction zone or to a point in the system downstream of said reaction zone or to both of these locations, the concentration of carbon monoxide and hydrocarbon present in the system in which said process is conducted being maintained sufficiently high during said process to prevent the existence of a flammable mixture in said system.

3. The process of claim 1 or claim 2, wherein said hydrocarbon is selected from aromatic hydrocarbons containing 6 to 10 carbon atoms and aliphatic hydrocarbons containing 2 to 6 carbon atoms.

4. The process of claim 1 or claim 2, wherein said oxygen-containing gas is substantially pure oxygen.

5. The process of claim 1 or claim 2, wherein said partial oxidation product is selected from cyclic anhydrides, alkylene oxides, halogenated hydrocarbons, aldehydes, unsaturated carboxylic acids, unsaturated nitriles and mixtures of these.

6. The process of claim 5, wherein said partial oxidation product is a cyclic anhydride and said hydrocarbon is an aromatic hydrocarbon containing 6 to 10 carbon atoms, a saturated or ethylenically unsaturated hydrocarbon containing 4 carbon atoms or mixtures of these.

7. The process of claim 6, wherein said cyclic anhydride is selected from phthalic anhydride, maleic anhydride or mixtures of these, and said hydrocarbon is selected from benzene, naphthalene, orthoxylene and four carbon straight-chain hydrocarbons.

8. The process of claim 5, wherein said partial oxidation product is selected from alkylene oxides, halogenated hydrocarbons, aldehydes, unsaturated carboxylic acids, unsaturated nitriles and mixtures of these and said hydrocarbon is a saturated or ethylenically unsaturated hydrocarbon containing 2 to 6 carbon atoms.

9. The process of claim 8, wherein said partial oxidation product is an alkylene oxide and said hydrocarbon is a straight-chain hydrocarbon containing 3 to 4 carbon atoms.

10. The process of claim 8, wherein said partial oxidation product is an aldehyde and said hydrocarbon contains 2 to 4 carbon atoms.

11. The process of claim 8, wherein said partial oxidation product is a halogenated hydrocarbon, said hydrocarbon contains 2 to 6 carbon atoms and a hydrogen halide is present in said reaction zone.

12. The process of claim 11, wherein said halogenated hydrocarbon is a chlorinated hydrocarbon having 2 to 4 carbon atoms and said hydrogen halide is hydrogen chloride.

13. The process of claim 8, wherein said partial oxidation product is an unsaturated carboxylic acid and said hydrocarbon contain 3 or 4 carbon atoms.

14. The process of claim 8, wherein said partial oxidation product is an unsaturated nitrile and said hydrocarbon contains 3 or 4 carbon atoms.

15. The process of claim 1 or claim 2, wherein the carbon dioxide is separated from said gaseous product by adsorption, absorption or membrane separation.

16. The process of claim 15, wherein the carbon dioxide is separated from said gaseous product by pressure swing adsorption.

17. The process of claim 16, wherein the unit in which said pressure swing adsorption is carried out contains an adsorbent selected from silica gel, molecular sieves and mixtures of these.

18. The process of claim 2, wherein one or both of the unreacted hydrocarbon and carbon monoxide are separated from said gaseous effluent by pressure swing adsorption.

19. The process of claim 18, wherein the unit in which said pressure swing adsorption is carried out contains an adsorbent selected from silica gel, molecular sieve and mixtures of these.

* * * * *